United States Patent [19]
Lyon et al.

[11] Patent Number: 5,897,503
[45] Date of Patent: Apr. 27, 1999

[54] ULTRASOUND TRANSDUCER PROBE HAVING CASE HANDLE GRIP SURFACES

[75] Inventors: Richard A. Lyon, Palo Alto; Richard W. Henderson, Fremont, both of Calif.; Robert Mesaros, Bozeman, Mont.; Vaughn R. Marian, Saratoga, Calif.

[73] Assignee: Acuson Corporation, Mountain View, Calif.

[21] Appl. No.: 08/910,568

[22] Filed: Aug. 1, 1997

[51] Int. Cl.⁶ ........................................................ A61B 8/00
[52] U.S. Cl. ............................................................ 600/459
[58] Field of Search .................................... 600/463, 459, 600/447, 437; 16/111 R; 73/629–632

[56] References Cited

U.S. PATENT DOCUMENTS

| | | | |
|---|---|---|---|
| 4,582,066 | 4/1986 | Barnes et al. | 128/661 |
| 4,969,231 | 11/1990 | Mader et al. | 16/111 R |
| 5,381,795 | 1/1995 | Nordgren et al. | 128/663.01 |
| 5,437,283 | 8/1995 | Ranalletta et al. | 600/463 |
| 5,505,205 | 4/1996 | Solomon et al. | 128/662.03 |
| 5,554,098 | 9/1996 | Yabe et al. | 600/121 |
| 5,681,263 | 10/1997 | Flesch | 600/141 |
| 5,690,113 | 11/1997 | Sliwa, Jr. et al. | 600/443 |
| 5,810,733 | 9/1998 | Van Creveld et al. | 600/459 |

Primary Examiner—Francis J. Jaworski
Attorney, Agent, or Firm—Hopkins & Carley

[57] ABSTRACT

A hand-held transducer probe is overlapped with elastomeric material for improving the friction and softness of the grip of the probe. The elastomeric material comprises a biocompatible material having a tear strength in excess of 110 pounds per inch and a hardness level less than approximately shore A 80. Also disclosed is a method of producing a hand-held transducer probe having an improved grip comprising the steps of assembling an acoustic array and cable assembly; attaching a handle portion over aid acoustic array and cable assembly; and attaching an elastomeric material over at least a portion of said handle portion.

30 Claims, 7 Drawing Sheets

ULTRASOUND TRANSDUCER PROBE HAVING CASE HANDLE GRIP SURFACES

FIELD OF THE INVENTION

This invention relates generally to ultrasound imaging equipment. In particular, it pertains to improving the grip of ultrasound transducers by applying an elastomer material onto a case handle during manufacture.

BACKGROUND OF THE INVENTION

Ultrasound imaging has become increasingly popular because of its ability to obtain images of internal body organs through non-invasive or minimally invasive techniques. Therefore, it is an ideal choice for many preliminary examinations, such as obstetrical or cardiology exams, and screenings for certain types of growth irregularities, such as tumors, without requiring substantial incisions.

Ultrasound imaging systems typically operate by transmitting ultrasound signals through a transducer which contains an array of piezoelectric elements capable of converting an applied voltage into mechanical motion and vice versa. In this way ultrasound acoustic signals can be transmitted into a medium where reflections, caused by impedance mismatches at acoustic interfaces within the medium, are received back at the transducer. Received acoustic signals are then converted back to electrical signals which are sent to a signal processor where, among other things, they are amplified and processed to construct visual image that can be displayed. The signal processor and display are generally a combine unit whereas the ultrasound transducer is typically in the form of a hand-held probe.

Transducer probes are manufactured in many different forms, including small diameter invasive tools such as catheters and endo-cavity probes. Non-invasive probes are usually palm size and hand-held, and are used, for example, in prenatal examinations of a fetus and in diagnosing cardiac health.

Figure 1:
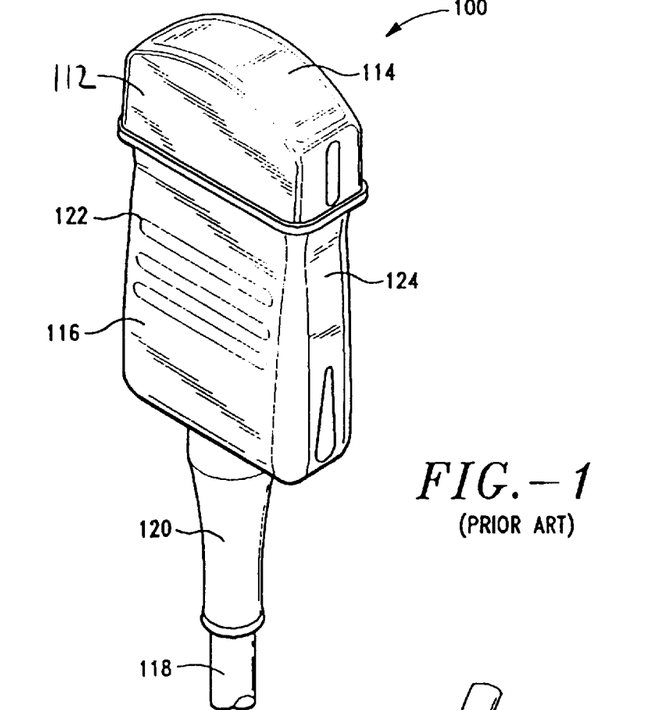
FIG. 1 is a perspective view of a prior art transducer probe assembly.

The manufacture of complex devices such hand-held transducer probes typically involves the integration of multiple components. FIG. 1 is a perspective view of a typical prior art hand-held transducer probe, generally referred by reference number 100. Transducer 100 is comprised of machined, cast or injection molded components including a nosepiece assembly 112, comprised of a plastic nosepiece and interior acoustic components, an acoustic lens or window 114, a plastic case handle 116 designed to be grasped by the user's hand, a flexible cable 118 for transmitting electrical signals to and from a signal processing unit (not shown), and a strain relief 120 for preventing cable 118 from fraying. Grip features 122, such as raised ribs or depressions are also shown. An alternative construction of case handles 116 comprises attaching together two clam shell-shaped or other part break-up case handle components.

Ultrasound technicians use transducer probes 100 for extended periods of time and utilize a variety of hand-hold positions. Technicians have experienced fatigue while holding onto the transducer probes 100, especially when wearing gloves and employing coupling gel. The variety of hand sizes and grip configurations of technicians cause difficulty in working with current transducer probes 100 for long periods of time. Once formed, rigid case handles 116 are relatively slippery and hard, thereby compounding grip problems for technicians if used alone. Many methods of improving the grip of case handles have been attempted with limited success. For example, increasing the friction of the case handle 116 has been tried by adding textured surfaces and/or raised ribs 122 and depressions to the case handle 116, but these adjustments did not improve the grip problems to the desired degree.

The grip features 122 of the prior art provide some improvement to a more secure grip of the probe 100 than when there are no grip features 122. Operator fatigue is an undesirable outcome of extensive use. Reducing operator fatigue is a favored usability quality.

Traditional transducer case handles 116 are made from the polysulfone, polycarbonate, or rigid polyurethane families of plastics. The case handle 116 material is chosen for structural strength, impact resistance and chemical resistance. The plastic case handle 116 materials employed in the prior art have a relatively low coefficient of friction and can feel slippery in the operator's hand, especially when gloves and gel are used by the ultrasonographer. These polymerics have good engineering properties, but are also hard and non-compliant. When the probe 100 feels slippery, technicians tend to hold the transducer 100 more tightly. The combination of a tight grip on a hard surface for an extended period of time exacerbates the problem of operator fatigue.

Recently, "ergonomic" transducer case handles 116 have been designed to reduce operator fatigue and discomfort by fitting to the human hand for the variety of applications and positions dictated to acquire ultrasound images. An example of such a handle is shown by Barnes et al. in U.S. Pat. No. 4,582,066.

U.S. Pat. No. 5,505,205, by Solomon et al., discloses elastomeric polymers employed as a transmissive interface over the acoustic window (see, for example, window 114 of FIG. 1) for conducting ultrasound energy from the transducer to a patient's body. The polymeric materials of Solomon are chosen so that the sound speed in the polymeric materials approximately matches the speed of sound and the impedance of the soft tissues in the human body. This is a highly specialized and expensive polymeric material. Moreover, this entire probe is not sealed and therefore only the nose piece is immersible in fluid to disinfect the probe. The probe cannot be fully immersed.

U.S. Pat. No. 5,381,795, by Nordgren et al., discloses a transducer design that uses a rubber-like encapsulated boot around the acoustic window of the probe to insulate the patient from the electrical connections to the transducer crystal and to permit immersion of the boot in a sterilizing liquid. The Nordgren patent teaches that the lower portion of the case closes around the boot.

Copending U.S. application Ser. No. 08/646,155 (abandoned), by Van Creveld et al., discloses a transducer probe design wherein a transducer acoustic assembly encapsulated with rubber-like acoustic lens or window material such as room temperature vulcanizing silicone rubber (RTV). The RTV compound forms both the lens and the case handle. There is no use of an underlying hard case handle material. While this copending application partially addresses the grip and comfort problems discussed above, it has certain aesthetic and functional disadvantages. The aesthetic disadvantage of complete encapsulation may limit the perceived functional goal of being a finely engineered medical device. The RTV or similar purpose material is chosen based on its ability to function as a transmissive interface for conducting ultrasound energy from the transducer to a patient's body. It is designed for low acoustic attenuation and for impedance that matches the impedance of body tissue. Preferred RTV compounds require accurate formulas to meet these and other non-acoustic needs, and therefore, are expensive and have relatively low tear strengths. This RTV-type material is also applied over a transducer probe assembly in a relatively expensive and time-consuming casting and curing process. Furthermore, complete coverage of the probe surface with RTV elastomer impedes smooth manipulation of the probe when placed against the patient's skin to obtain an ultrasound reading.

Accordingly, there exists a need for a transducer probe that allows the operator to grip the transducer more comfortably and securely than previously possible while also facilitating desired smooth manipulation in rotating and translating probe position while the probe is placed against a patient's skin.

There also exists a need for a transducer probe that is liquid tight for complete immersion disinfecting fluid.

There also exists a need for a transducer probe grip surface design which can be personalized in size, shape and color design.

There also exists a need for a transducer probe design which can be manufactured at lower cost and with robust, high tear strength materials which will survive mechanical abuse.

SUMMARY OF THE INVENTION

The present invention substantially reduces or overcomes all of the above problems associated with the prior art by providing a hand-held transducer probe having a grip that is ergonomic, soft, has increased friction for more secure gripping, allows smooth manipulation in rotating and translating probe position while it is placed against a patient's skin, has a low manufacturing cost, is suitable for mass production, can be personalized, allows the entire transducer probe to be sealed for immersion in fluid up to and including the strain relief, is not degraded or discolored by harsh disinfectants, and which stands up to significant mechanical abuse.

The present invention includes transducer probes having a hard case handle and at least one elastomeric compound applied over at least a portion of the case handle. Preferred locations of the elastomeric material over the case handle are positions where ultrasound technicians tend to grip the surfaces of the case handle most frequently, herein called the "gripping positions." After being placed on the gripping positions the elastomeric compounds are called "grip surfaces." The elastomeric material is chosen for providing higher friction and a softer grip at the griping position than is provided by the hard case handles alone. The addition of the elastomeric material permits the operator of the probe to grip the transducer more comfortably and securely when compared to gripping traditional case handles 116. The elastomeric material is also chosen for many important, and sometimes competing, properties, for example, optimal biocompatibility, mechanical strength, durability, aesthetic properties, and chemical resistance.

In another embodiment of the invention the elastomeric material is manufactured as elastomeric accessories attachable to any previously manufactured transducer probe.

Also disclosed is a method of producing a hand-held ultrasound transducer probe. In accordance with one method of the present invention, an acoustic array and a cable assembly are assembled, a hard case handle is attached over the acoustic array and cable assembly, and an elastomeric material is attached over at least a potion of the case handle, preferably on the gripping positions.

In another embodiment, the case handle is formed from two clam shell shaped components. Each clam shell shaped component is formed with small perforations at the gripping positions. Elastomeric compounds are injection molded or cast onto the gripping positions such that the elastomeric material penetrates the perforations of the case handle. The elastomeric material that penetrates the perforations spreads and solidifies, thus forming a mechanical anchor on the inside of the clam shell shaped components. The case handle having elastomeric material anchored to it is then assembled with standard probe components.

Also disclosed is a method of improving the grip of a hand-held ultrasound transducer probe. In accordance with one method of the present invention, hard case handle components are overlapped with an elastomeric material. The elastomeric material may take many forms, including elastic bands, adhesive tape, heat shrink material, and self-adhesive elastomeric pads.

Preferred types of elastomeric compounds include polyolefin based compounds, rubber based compounds, low durometer polyurethane based compounds, foam-based compounds, polyvinylchloride (PVC) based compounds and other rubber-like elastomeric materials. The elastomeric compounds employed in this invention have better mechanical properties, friction, tear strength, stain resistance, abrasion resistance and lower cost than the more expensive custom formulated RTV and polyurethane compounds used over prior art acoustic windows 114 of transducers 100.

An advantage of the present invention is its versatility. The elastomeric compounds, i.e., the "case handle grip surfaces," can be molded or cast onto a case handle of the present invention or can be attached to any type of prior art case handle 116. This is true whether the case handle comprises multiple pieces or one piece and whether or not the probe will be immersed in harsh disinfectant. The case handle grip surfaces can be placed in any location desired on the case handle, and cover any percentage of the case handle desired.

Another advantage is that the case handle grip surfaces can be permanent or disposable.

Another advantage is that the case handle grip surfaces can allow service to the probe.

Another advantage is that the case handle grip surfaces can be of different sizes or shapes to modify the case handles to accommodate different clinical applications or hand sizes.

Another advantage is that a combination of several different types of case handle grip surface materials can be applied on a single transducer probe, and only in the places desired.

Another advantage of the case handle grip surfaces is that many methods of attachment are available, including, but not limited to, thermoplastic over molding, injection molding, casting, dipping, compression molding, heat shrink tubing and adhesion.

Another advantage is that the case handle grip surfaces can accommodate graphic elements and can be designed to not interfere with graphic elements for identifying the transducer probe.

Another advantage is that the manufacture of transducer probes having the case handle grip surfaces is amenable to low cost, rapid mass production and individual personalization processes.

Another advantage is that the preferred material forming the case handle of the probe of the invention is reliable, durable and doesn't sustain damage and protects internal components from damage when impacting other surfaces.

These and other advantages will become apparent upon reading the following detailed descriptions and studying the various figures of the drawings.

BRIEF DESCRIPTION OF THE DRAWINGS

The invention, together with further objects and advantages thereof, may best be understood by reference to the following description taken in conjunction with the accompanying drawings in which:

FIG. 10A–C is a side view of an injection molding process of forming the elastomeric grip surfaces over the gripping positions of the case handle and two methods of mechanical interlock of the elastomeric material onto the gripping positions;

FIGS. 11A–F illustrate customization of the case handle for more secure gripping for technicians having larger hands by increasing the thickness of the elastomeric grip surfaces;

DETAILED DESCRIPTION OF THE PREFERRED EMBODIMENTS

In accordance with an embodiment of the present invention, a transducer having an improved grip and method of improving the grip of a transducer will be described herein. The basic functional components of the transducer described in relation to the prior art shown in FIG. 1 comprising an acoustic lens/window 114, a piezoelectric stack array (not shown, located underneath acoustic lens), nosepiece assembly 112, case handle 116, cable strain relief 120, and cable assembly 118 are also included in the preferred embodiment. The nose piece assembly 112 may include the case handle 116 in one embodiment.

Figure 2:
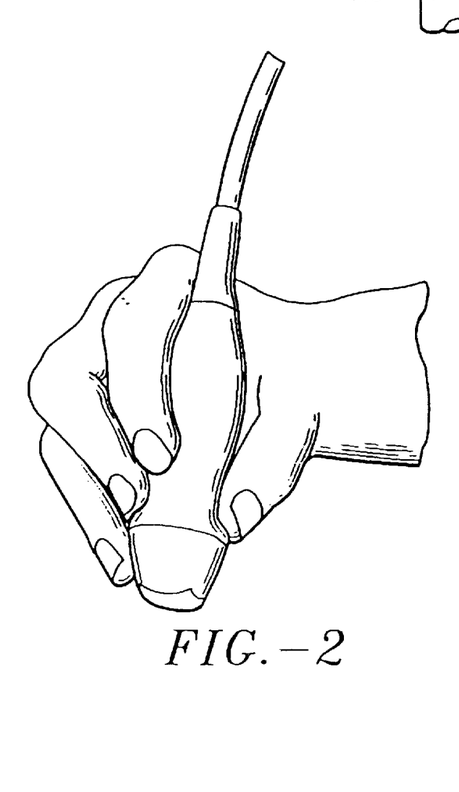
FIGS. 2 and 3 illustrate two hand grip positions for holding transducer probes.
Figure 3:
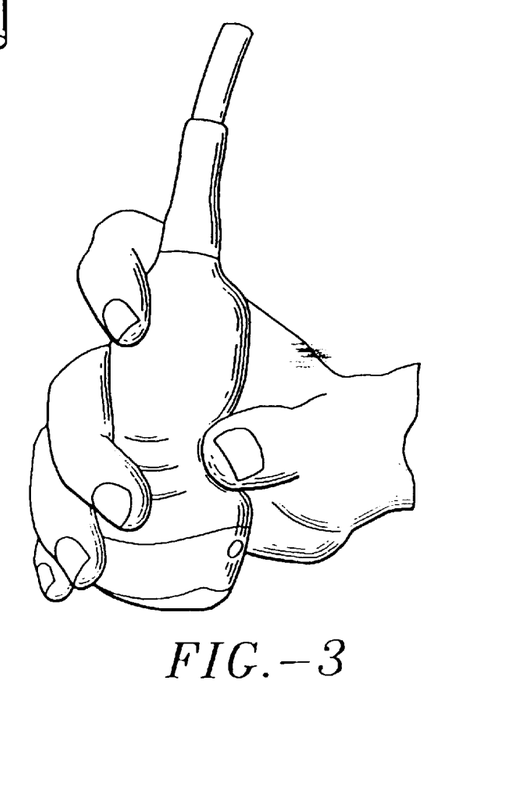

FIGS. 2 and 3 illustrate two common hand grip positions employed by ultrasound technicians. In FIG. 2 the thumb and middle fingers are holding a cardiology transducer on the sides of the case handle near the nose piece, with forefinger on the top edge. In FIG. 3 the technician's forefinger rests near the cable, while the sides and edges of this general imaging transducer are held by the fingers and thumb. These and other hand grip positions have helped determine the optimum placement of the elastomeric material over the case handle portion of the present invention.

Figure 4A:
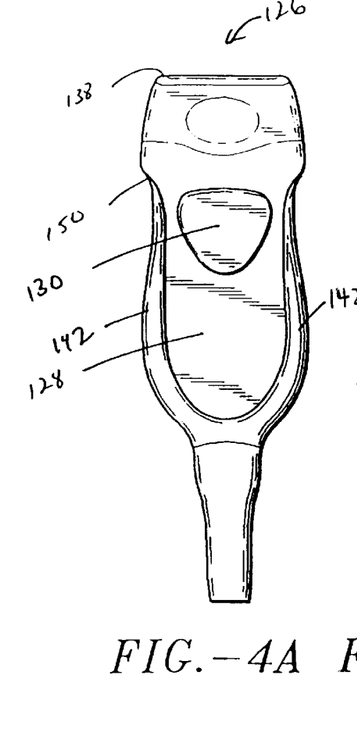
FIGS. 4A and 4B are a front and side view of a preferred embodiment of the present invention wherein the hard case handle is overlapped by an elastomeric material.
Figures 4B, 5:
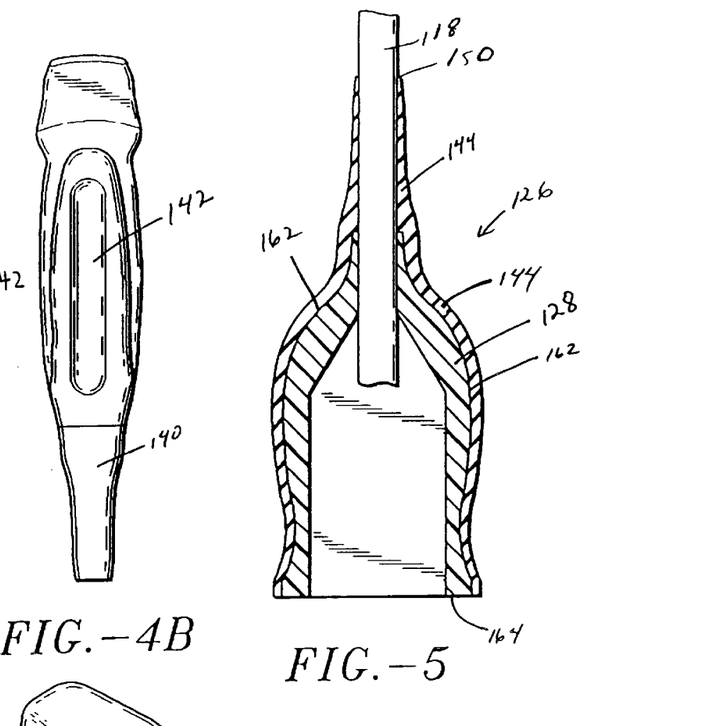
FIG. 5 is a cross sectional view of a preferred embodiment of this invention employing a strain relief that is integral with the case handle grip surfaces over the case handle.

FIG. 4 illustrates a preferred embodiment of a transducer probe of the present invention, generally denoted by the numeral 126. In the present invention an elastomeric compound is molded over at least a portion or all of the handle portions of the front and back gripping positions of the transducer handle portion 128 or handle portion components forming front and back grip surfaces 130. The elastomeric compound is also molded over at least a portion of the side gripping positions of the handle portion 128 forming side grip surfaces 142. The elastomeric material provides increased friction and a softer grip for grasping and manipulating said handle portion than is provided by said handle portion alone. The strain relief 140 may be the same as or a different material from side grip surfaces 142.

Construction of this invention begins as standard in the art: an acoustic array is constructed and pre-tested; a cable assembly is built and attached to the array, along with any thermal treatment, mechanical supports, shielding, and any other switches, indicators, strain reliefs or additional components.

Next, the handle portion 128 is attached or formed in place. At this point the case handle portion 128 of the present invention may or may not have the elastomeric material 130, 142 overlaid, as described below.

Several versions of handle portion 128 construction and attachment that are standard in the art are employable with this invention. The handle portion 128 may be fabricated as a single piece of rigid or semi-rigid base material by injection molding, casting, machining, etc. In a preferred embodiment the handle portion 128 is fabricated in several sections, such as "clam shells" or single piece construction of rigid or semi rigid base material by injection molding, casting, machining, etc., to be later joined if necessary in an assembly operation.

Preferred properties of the handle portion 128 material are impact and chemical resistance. Additionally, the melt flow temperature of the handle portion 128 material is preferred to at least 20° C. higher than the elastomeric material mold or casting temperature in order to mold or cast the elastomeric material over the handle portion 128. Case handle materials that are standard in the art are employable with the present invention.

In a preferred embodiment, the case handle 128 is injection molded and is a polysulfone material. A preferred polysulfone material is Radel, a polyethersulfone purchased from Amoco. Another preferred compound employed to fabricate the case handle 128 is a rigid injection moldable or castable polyurethane.

FIG. 5 is a cross sectional view of a preferred embodiment of this invention employing a strain relief 144 that is integral with the case handle grip surfaces 144 over the case handle 128. The strain relief may be the same or different material as the grip surfaces. Here, a transducer probe case handle 128 is completely covered with the elastomeric material 144. Also illustrated are cable 118, cable to strain relief bond 150, hard case material 128, and the line of demarcation 162 between the hard case 128 and the overlapping elastomer 144 wherein an adhesive, such as a "B" stage adhesive, is laid prior to overlaying the elastomeric material 144. Preferred B stage adhesives have bond strengths of greater than 100 psi on a lap shear test. A preferred B stage adhesive is Bostik 7119M polyurethane solvent adhesive (available from Bostik, phone number 206-271-5993). The B-stage adhesive is activated at molding temperatures of the elastomeric material, such as PVC, within the range of 80° C. to 90° C., providing a tenacious bond between the case handle 128 and the PVC. Here, the nose piece and acoustic window (not shown) are standard in the art for allowing smooth manipulation of the window against the patient's skin. The nose piece is attached to the case 128 at joint 164 as is standard in the art.

Preferred elastomeric compounds have been tested for optimal biocompatibility; hardness; chemical resistance to disinfectants, bleach, alcohol and staining from iodine; adhesion to handle portions 128; and for tear strength in excess of 110 pounds per inch. The preferred elastomers are also environmentally resistant; are abrasion resistant; have a melt temperature lower than that of said handle portion; have a hardness level below a range of shore A 80; are injection moldable or castable; have a coefficient of friction exceeding that of said handle portion; have lap shear strength; have resistance to UV light, humidity and temperature extremes;and have shrinkage and abrasion resistance. Preferred compounds are also chosen for optimal injection molding properties for low cost mass production, for ease of manufacture, raw material cost, coefficient of friction, preferred mold temperature, and the ability for color matching for aesthetic purposes. The grip of these materials must not be slippery when gel-soaked.

Preferably the die B dumbbell tear strength of the elastomeric material is greater than 110 pounds per inch (per ASTM D624) and the hardness level is less than approximately shore A 80 and more preferably within the range of approximately shore A 40 to 70. The tensile strength is preferably greater than 700 pounds per square inch, using test standard ASTM D412.

Each of these properties is important to the present invention. For example, in a hospital setting, transducer probes 126 are immersed in chemical disinfectants, such as alcohol and iodine compounds to eliminate biological contamination. However, iodine tends to stain elastomers a reddish brown color, and alcohol immersion is not recommended for urethanes, which, as previously mentioned, are employed as lens materials. Some urethanes tend to swell or become "sticky" or lose substantial mechanical strength if exposed to alcohol. Because of the acoustic need for lenses, and window surfaces, urethanes are still employed for these purposes. However, a grip material must withstand alcohol wipe and retain high peel strength and tear strength and not become "sticky."

Materials employed in the present invention may be purchased in bulk and cost approximately one tenth the cost of RTV or polyurethanes that have been optimized for acoustic properties.

The elastomeric materials of the invention may be employed in single layers or in multilayers incorporating non-sliding surfaces.

Some of the preferred elastomeric compounds for providing the desirable amount of friction and soft feel of the present invention are polyolefin based materials, rubber based materials, low durometer polyurethane based materials, polyvinylchloride (PVC), foam-like materials and other rubber-like elastomeric materials. As used herein, the term "foam-like" is meant to mean materials that contain air. These materials include, for example, neoprene, a wet suit material.

Some of the preferred materials include QST, Inc.'s Monprene MP 1726 and MP1714 polyolefins, and Diamond Polymer Inc.'s Softflex 0615 and Softflex 0921. QST, Inc. is based in St. Albans, Vt. In a preferred embodiment, the Softflex compounds are pre-dried. Diamond Polymer, Inc. is based in Akron, Ohio. The recommended processing guidelines provided with the purchase of each compound should be followed when used these compounds for this invention.

Another preferred compound is the HTE 3060, a PVC-nitrile, hereinafter referred to as PVC. PVC bonds well to a preferred casing material, Radel, especially when used in conjunction with an adhesive, such as a B stage adhesive.

If the case handle 128 is made of multiple components, then the next step is to join the components by adhesives, R.F. welding, ultrasound welding, ultra violet cured, adhesive, thermal welding, solvent bonding, snap fit, mechanical fasteners, or other combination of appropriate processes standard in the art. Preferred adhesives for joining components include, but are not limited to, Schul Int. Plasti-Loc 8, Shell Epon 160 Epicure 3274, and 3M DP420, chosen for the strength of the bonds, optimized viscosity for use, biocompatibility and the submersible liquid tight seal provided. If not already done, the case handle 128 is then attached to the acoustic array or other contact/nosepiece portions, strain reliefs, or additional components. All additional steps are also performed at this time, such as back-potting and/or sealing the case handle 128 together, as required by the method chosen and as are standard in the art.

Upon completed assembly, the present invention is "fully" immersible in fluid, that is, it is immersible up to, and including, the strain relief 120. Each seam has a liquid tight seal by employing o-rings, epoxies and glues around areas that may possibly leak, such as screws. PVC and epoxy glue are also employed to make liquid tight joints.

Next, if desired, additional elastomeric compound is now added onto all or part of the case handle 128 of the assembled transducer by casting, dipping, heat shrink tubing, adhesive, or other appropriate method. Although the elastomers forming the grip surfaces 130, 142 may be overmolded on another elastomer, it is preferably mounted directly over the case handle 128 material.

In a preferred embodiment of the invention, elastomeric material is overmolded only over the gripping positions 132, 134. This allows the nosepiece portion around the acoustic window 138 to remain as a slick surface against the body for ease of obtaining ultrasound images and for high mechanical strength. The non-gripping positions of the case handle 128 are also preferably left without elastomer so that the technician's fingers can easily slide along the smooth surfaces of the case handle 128 when changing grip positions. This facilitates smooth manipulation in rotating and translating probe 126 position while it is placed against the patient's skin.

The forms of attachment of the elastomer material to the case handle portion 128 at the gripping positions 132, 134 may include, but are not limited to, injection molding, casting, dipping, heat shrinking, adhering, stretching an elastomeric material over the case handle 128, attaching a belt-like piece over the handle portion 128 via snaps, Velcro™, etc. The attachment of the elastomeric material may be permanent, semi-permanent or removable, replaceable or serviceable, disposable or may be the attachment of an accessory component. In a preferred embodiment, the elastomer material is overmolded to the case handle 128 in a standard thermoplastic molding process. In another embodiment, features are incorporated on the probe surface to grasp or lock with the elastomeric material.

Desired graphics may be applied to identify the transducer probe 126 in a variety of methods. For example, incremental means of color or icon-coding the elastomeric materials applied to the transducers may be employed. Inexpensive logos or name personalization may be employed.

When a sonographer custom orders a probe, customized features may be chosen from the group comprising a different elastomeric material in each layer of a multilayer grip surface for varying the pliability of the grip, width of grip, color and design of grip surfaces, types of ergonomic features and means of attaching or fastening the grip surfaces, such as with Velcro™—type materials or snaps. An elastomeric band may be fastened around the probe with the fasteners as either part of the band or with a fastener on the probe and a mating fastener on the band.

Figure 6:
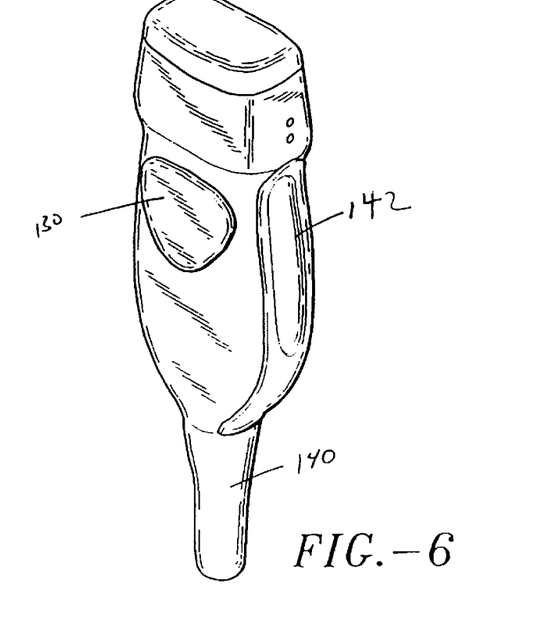
FIG. 6 is a perspective view of a preferred embodiment of the present invention wherein the hard case handle is overlapped by an elastomeric material.

FIG. 6 is a perspective view of a preferred embodiment of the present invention wherein side grip surfaces 142 are not integral with strain relief 140 or each other.

Figure 7A:
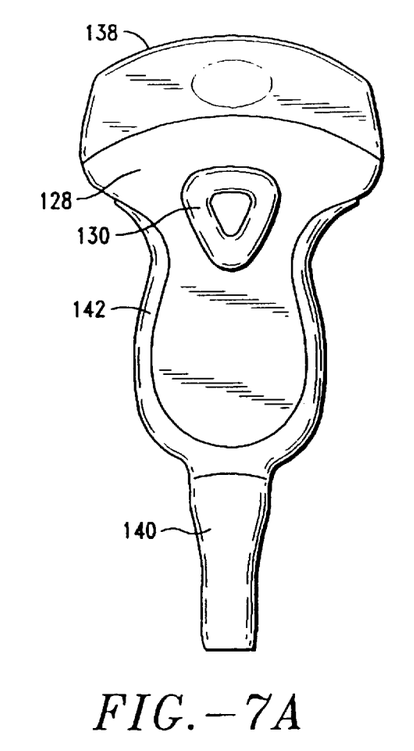
FIGS. 7A and 7B are front and side views of a preferred embodiment of this invention for a larger transducer.
Figure 7B:
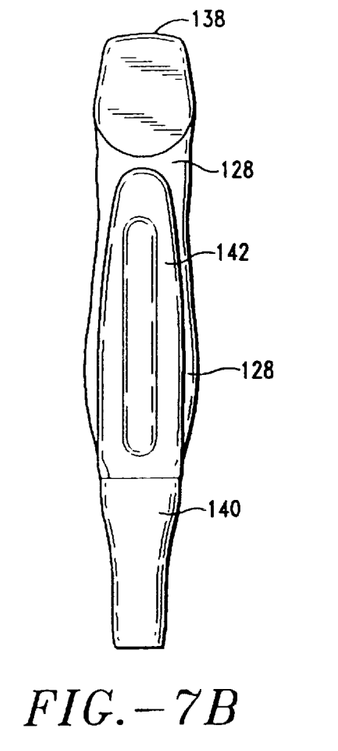

FIGS. 7A and 7B are front and side views of a preferred embodiment of this invention of a larger transducer. In FIG. 7, the strain relief 140 is made of a different elastomeric material than the elastomeric grip surfaces 130, 142, such as PVC or silicon rubber material. PVC and silicon rubber have more durable properties desired in a continually flexed strain relief 140. The strain relief 140 in this embodiment is PVC molded onto a polysulfone case handle 128 component. The PVC strain relief 140 is then solvent bonded the PVC cable 118 for a liquid tight seal with the cable 118. In an alternative embodiment, the strain relief 140 is made of the same material as the grip surfaces 130, 142.

Figure 8:
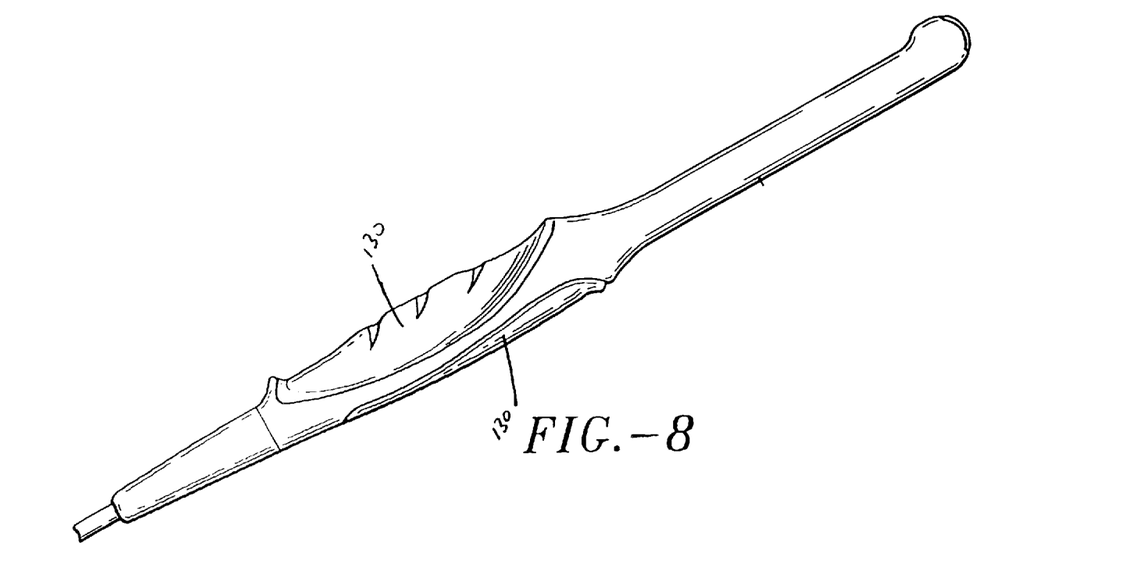
FIG. 8 illustrates preferred positions of the elastomeric material on an endo-rectal or endo-vaginal probe.

FIG. 8 illustrates a preferred position of the elastomeric material grip surfaces 130 on the gripping positions of an endo-rectal or vaginal probe. Places to rest the fingers have been designed into these grip surfaces 130.

Figure 9:
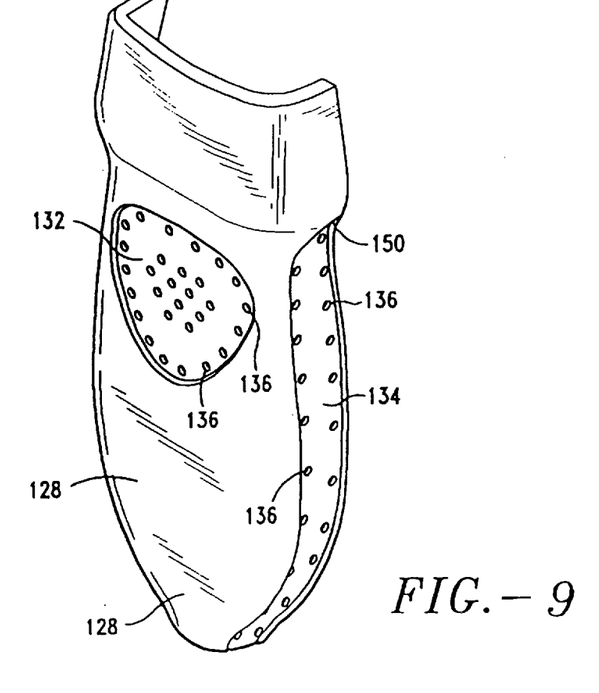
FIG. 9 is a perspective view of one-half of a case handle having indentations and holes at the gripping positions.

Referring now to FIG. 9, an embodiment of one-half of a handle portion 128 having a clam shell shape is shown. In a preferred embodiment, the case handle portion 128 is manufactured having indentations at the gripping positions 132, 134 in anticipation of the elastomeric material overlay forming grip surfaces 130, 142. In another preferred embodiment, the gripping positions 132, 134 also have perforations 136 that allow elastomeric material to penetrate the case handle portion 128 in order to better adhere the elastomeric material to the gripping positions 132, 134 and prevent the elastomeric material from peeling off of the case handle portion 128.

In a preferred embodiment illustrated in FIG. 10A–C, the elastomer is mechanically anchored to the case handle 128. In some processes, such as injection molding, perforations 136 allow the fluid elastomeric material 135 to penetrate the case handle 128 when it is applied. The fluid elastomeric material 135 is "backed up" by additional elastomeric material on the inside of the case handle 128, thereby providing either a mechanical interlock 146 of the elastomeric material or a mechanical anchor 148. The perforations 136 can be any shape necessary to allow penetration and interlocking 146 or anchoring 148 of the elastomeric material through the case handle 128. For example, the perforations 136 may be holes or slots having diameters or lengths of approximately 1–2 mm. However, the perforations 136 cannot be too large nor can their concentration be too dense or interference with the impact resistance of the hard case handle 128 may result.

The perforations 136 may be particularly useful around the edges of the gripping position indentations 132, 134 to reinforce the mechanical interlock 146 or to add anchoring 148 to prevent peeling away of the grip surfaces 130, 142 at the seams 150. Generally, no additional adhesive is needed with this method of overlaying the elastomeric material onto the handle portion 128, because the interlocking 146 or anchoring 148 as well as the adhesive action of the over-molding process allows the elastomeric material to adhere with great tenacity to the handle portion 128.

In another embodiment, the case handle 128 is attached and/or formed over the assembled acoustic array and cable assembly and then the elastomeric material is over molded. Under these circumstances, there are heat limitations with the overlaying process, as too much heat may destroy the acoustic stack. If desired, an adhesive may be applied to the case handle 128 prior to molding to facilitate bonding of the elastomer during molding. Preferred adhesives are "B stage" adhesives having bond strengths of greater than 100 psi on a lap shear test. A preferred B stage adhesive is Bostik 7119M polyurethane solvent adhesive (described earlier) activated within the range of 80° C. to 90° C.

Figure 11A:
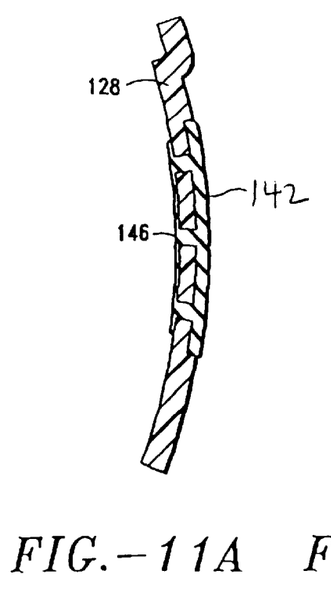
Figure 11B:
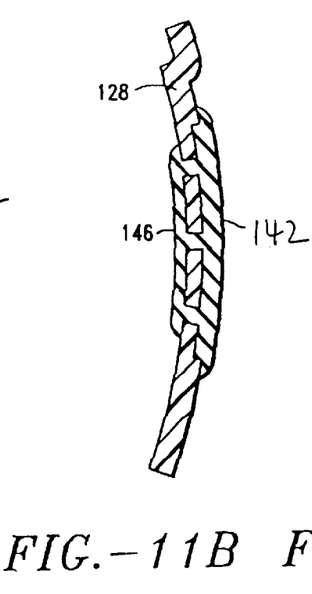
Figure 11C:
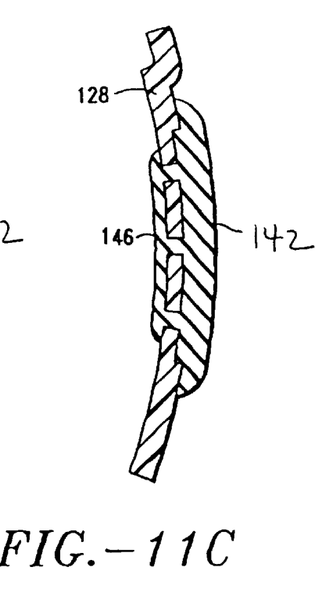
Figure 11D:
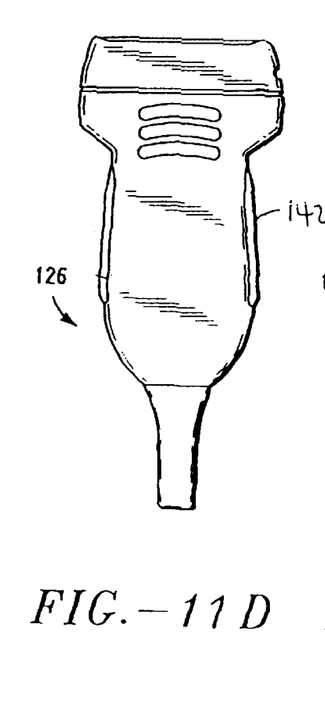
Figure 11E:
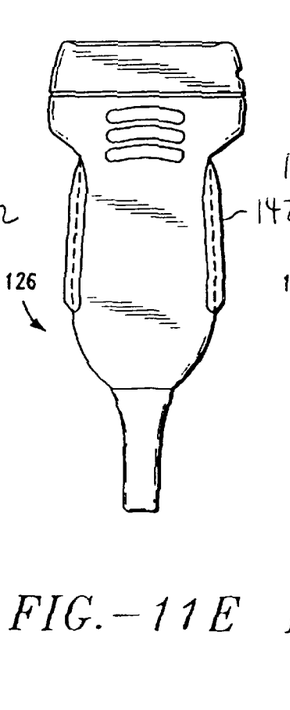
Figure 11F:
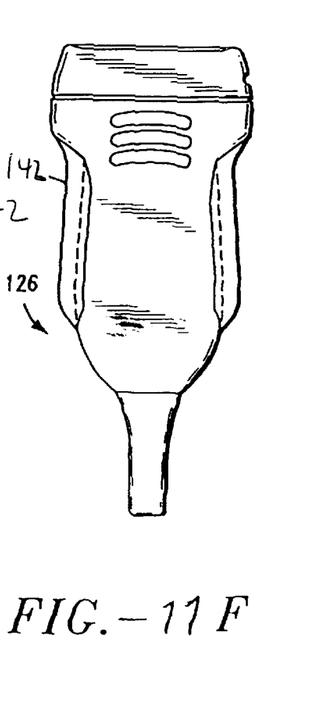

In another embodiment of the invention illustrated in FIGS. 11A–F, the width of the probe 126 is increased by increasing the amount of the case handle grip surfaces 130, 142, in order for the probe 126 to fit and accommodate various hand sizes and grip configurations. While being applied, the thickness of the fluid elastomeric material 135 is increased within a range of 0.5 to 10 mm for forming thicker grip surfaces 130, 142 per case handle 128. Preferable grip surfaces 130, 142 are within a range of 1 to 5 mm extra elastomeric material per side. FIGS. 11A, B and C are side views of a clam shell shaped case handle 128 component, illustrating the mechanical interlocking 146 of the elastomeric material on the inside of the case handle 128 and the progressively increasing width of side elastomeric material grip surfaces 142. FIGS. 11D, E and F are front views of the probe 126 illustrating progressively wider case handles 128 as the amount of fluid elastomer 135 is increased and solidified into side grip surfaces 142.

Figure 12:
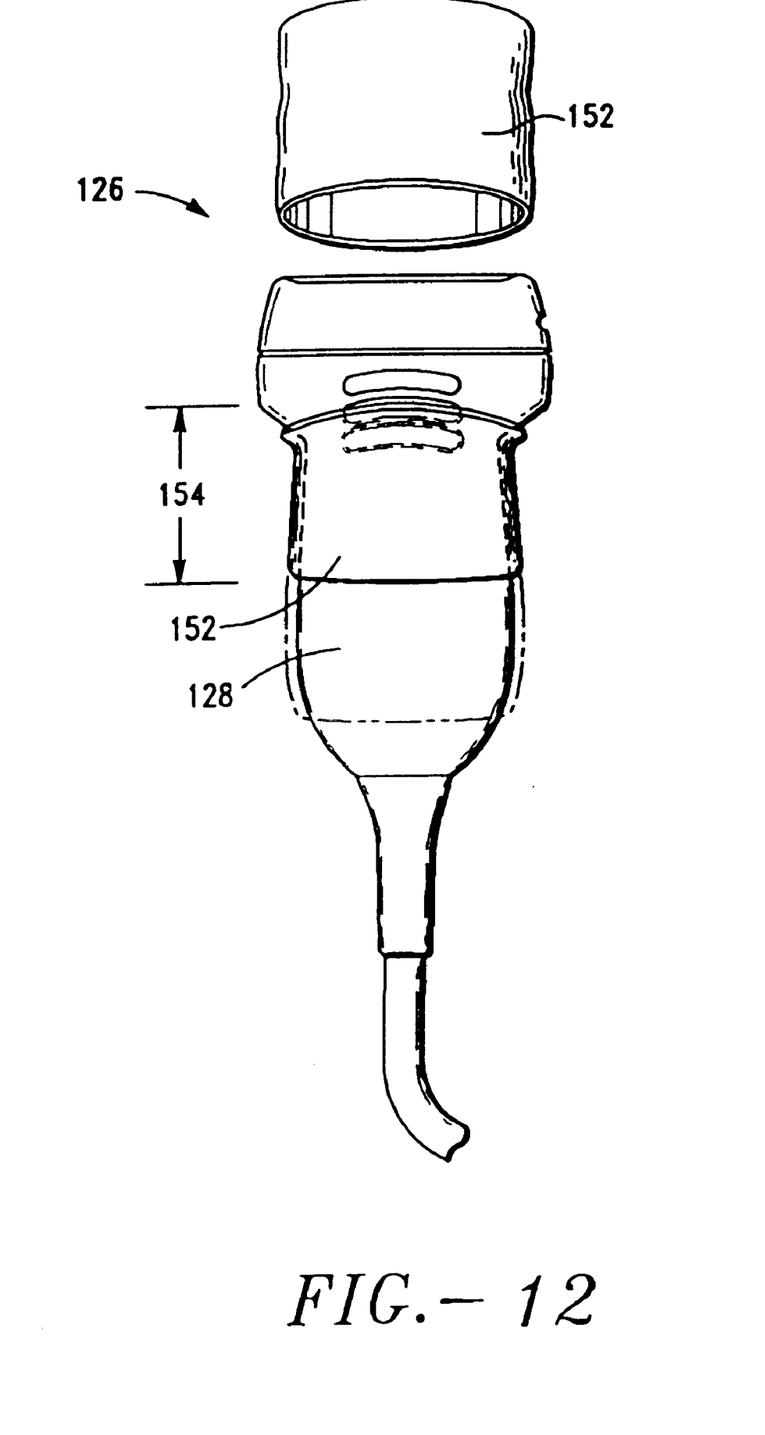
FIG. 12 is a front view of a transducer probe having an elastic sleeve or shroud or attached around the case handle.

Referring now to FIG. 12, a front view of a transducer case handle 128 having an elastic band or sleeve 152 made of the elastomeric compounds of this invention stretched over the case handle 128 is shown. The elastic band 152 is designed as a particular accessory to a particular probe 126 to fit the shape of a particular transducer and hand-size. This band 152 may also be attached around the probe handle with Velcro™—type fasteners, snaps, etc. The band 152 may cover a smaller or larger surface area of the case handle 128 by increasing or decreasing width 154.

In another embodiment of the invention, the band 152 is comprised of heat shrink tubing. The band 152 is placed around a probe case handle 128. Heat is applied in order to shrink the band 152. In another embodiment the back of the band 152 has adhesive and the heat causes the adhesive to bond the band 152 to the probe case handle 128.

As with all elastomers of the invention, the bands 152 may be disposable or permanent, cleanable in disinfectant and amenable to color coding and other types of personalization. The bands 152 may be textured and/or have sculpted surfaces such as natural places for fingers to rest. These bands 152 may be molded to form to the transducer probe 126 or die-cut from a foam sheet. Optional features may be incorporated on the probe surface to grasp or lock the band 152.

Figure 13:
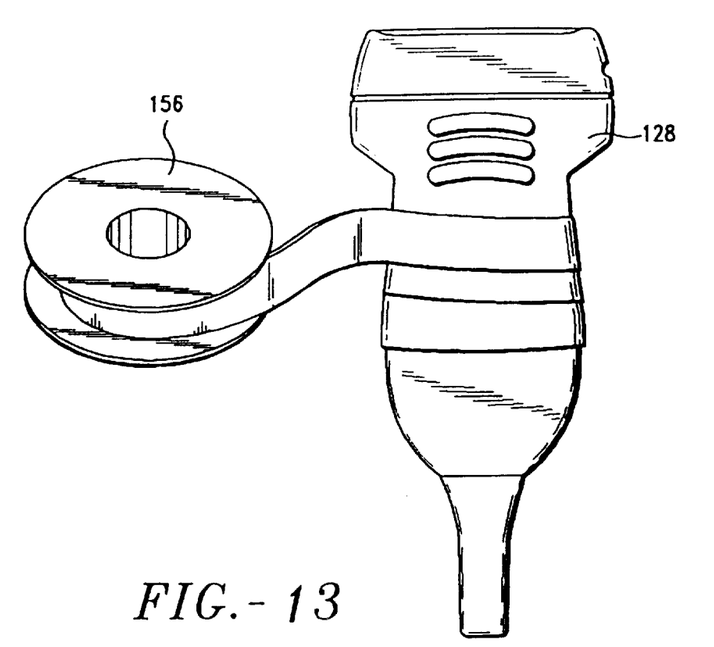
FIGS. 13 and 14 illustrate the use of elastomeric tape and self adhesive pads around or on the case handle.
Figure 14:
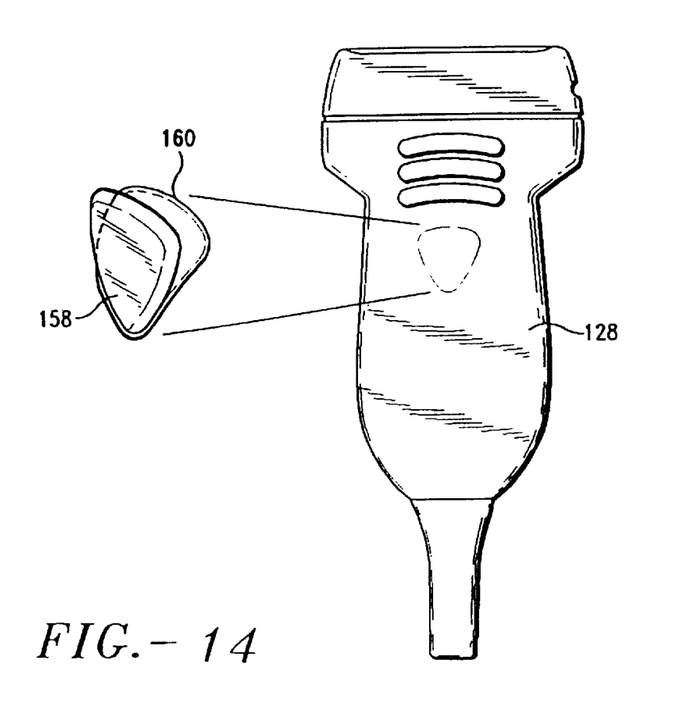

Referring now to FIGS. 13 and 14, the difference between adhesive tape and adhesive pads is illustrated. The elastomeric material may be manufactured in the form of a roll of tape 156. When the adhesive tape of the invention is used, as shown if FIG. 13, an appropriate amount of elastomer may be wrapped around the case handle 128 to customize width and pliability. The size, friction and softness of the case handle 128 may be varied by individual users on an as-needed basis by adding or decreasing the tape.

Self-adhesive pads 158 shown in FIG. 14 can be manufactured in precut sizes or in large sheets, wherein the purchaser may cut the size and shape desired. Adhesive pads 158 have peelable backing 160. Alternatively, the pads 158 are not self-adhesive, and may be applied to the case handle 128 with a permanent adhesive, such as an epoxy, or a removable adhesive such as contact cement or transfer adhesive.

Although the foregoing invention has been described in some detail by way of illustration and example for purposes of clarity and understanding, it will be obvious that certain combinations, changes and modifications may be practiced within the scope of the appended claims. Particularly, the invention relates to employing a durable material for manufacturing a transducer case handle and overlaying elastomers to provide a more secure and ergonomic grip. The gripping materials provide adequate friction and softness even with the use of gloves and gels, thereby providing more comfort and effectiveness in acquiring an ultrasound image with less fatigue to the technician.

What is claimed is:

1. A hand-held ultrasound transducer probe comprising:
   a housing having an ultrasound transducer mounted therein, said housing including:
      a handle portion for being grasped by the user to manipulate said transducer probe; and
      an elastomeric material overlapping at least a portion of said handle portion, said elastomeric material being a separate component from said handle portion and being attached to said handle portion:
      wherein said elastomeric material provides increased friction and a softer grip for grasping and manipulating said handle portion than is provided by said handle portion alone.

2. The ultrasound transducer probe as recited in claim 1 wherein said handle portion has gripping positions and said elastomeric material is attached to at least a portion of said gripping positions.

3. The ultrasound transducer probe as recited in claim 2 wherein said elastomeric material is selected from the group consisting of polyolefin based materials, rubber based materials, polyurethane based materials and blends of these materials.

4. The ultrasound transducer probe as recited in claim 3 wherein said elastomeric material is selected from the group further consisting of polyvinylchloride, silicone rubber, and neoprene-type materials, and blends of these materials.

5. The ultrasound transducer probe as recited in claim 1 wherein said elastomeric material is biocompatible, has a die B dumbbell tear strength in excess of 110 pounds per inch, and has a hardness level less than approximately shore A 80.

6. The ultrasound transducer probe as recited in claim 5 wherein said elastomeric material is colorable.

7. The ultrasound transducer probe as recited in claim 5 wherein said elastomeric material has a tensile strength greater than 700 pounds per square inch.

8. The ultrasound transducer probe as recited in claim 5 wherein said hardness level of said elastomeric material is within the range of approximately shore A 40 to 70.

9. The ultrasound transducer probe as recited in claim 5 wherein two or more distinct sections of said elastomeric material are attached to said handle portion.

10. The ultrasound transducer probe as recited in claim 5 wherein said elastomeric material has a thickness within the range of approximately 0.5–10 mm.

11. The ultrasound transducer probe as recited in claim 10 wherein said elastomeric material has a thickness within the range of approximately 1–5 mm.

12. The ultrasound transducer probe as recited in claim 5 wherein said elastomeric material is a self-adhesive elastomeric pad.

13. The ultrasound transducer probe as recited in claim 5 wherein said elastomeric material is a self-adhesive tape.

14. The ultrasound transducer probe as recited in claim 5 wherein said elastomeric material further comprises a thermally activated adhesive.

15. The ultrasound transducer probe as recited in claim 5 wherein said elastomeric material is an elastic band.

16. The ultrasound transducer probe as recited in claim 5 wherein said elastomeric material is a heat shrink band.

17. The ultrasound transducer probe as recited in claim 16 wherein said heat shrink band further comprises heat activated adhesive for bonding said heat shrink band to said ultrasound transducer probe.

18. The ultrasound transducer probe as recited in claim 5 wherein said transducer probe further comprises a strain relief and said elastomeric material is attached in one substantially continuous piece covering a substantial portion of said handle portion and said strain relief.

19. The ultrasound transducer probe as recited in claim 1 wherein said handle portion comprises a hard, durable polymeric material.

20. The ultrasound transducer probe as recited in claim 19 wherein said handle portion is selected from the group consisting of polyethersulfone, polycarbonate, polyurethane, polysulfone, PET and families thereof.

21. A method of producing a hand-held ultrasound transducer probe comprising the steps:
   assembling an acoustic array and cable assembly;
   attaching a handle portion over said acoustic array and cable assembly; and
   attaching an elastomeric material over at least a portion of said handle portion, with an adhesive being employed between said handle portion and said elastomeric material to assist in securing said elastomeric material to said handle portion,
   wherein said elastomeric material provides increased friction and a softer grip for holding said transducer probe than is provided by said handle portion alone.

22. The method of claim 21 wherein said elastomeric material is attached to said handle portion by thermoplastic overmolding.

23. The method of claim 21 wherein said elastomeric material is attached to said handle portion by casting.

24. The method of claim 21 wherein said handle portion has gripping positions and said elastomeric material are attached over at least a portion of said gripping positions.

25. The method of claim 24 wherein said handle portion is formed with indentations at said gripping positions for assisting in securing said elastomeric material to said gripping positions.

26. The method of claim 25 wherein said handle portion has an inside surface and an outside surface, said outside surface including said gripping positions, said elastomeric material being in a liquid phase when said elastomeric material is applied to said gripping positions of said handle portion, said handle portion being formed with perforations in said gripping positions for allowing said elastomeric material to pass through Said perforations when said liquid elastomeric material is applied to said gripping positions for allowing said elastomeric material to solidify on both the inside and outside surfaces of said handle portion for assisting in securing said elastomeric material to said handle portion.

27. The method of claim 21 wherein said elastomeric material is attached to said handle portion before said handle portion is attached to said acoustic array and cable assembly.

28. The method of claim 21 wherein said handle portion is produced over said acoustic array and cable assembly.

29. The method of claim 21 wherein said adhesive is a polyurethane.

30. The method of claim 29 wherein said polyurethane is a heat activated adhesive.

* * * * *